(12) United States Patent
Teles et al.

(10) Patent No.: US 8,575,379 B2
(45) Date of Patent: Nov. 5, 2013

(54) PROCESS AND DEVICE FOR THE OXIDATION OF ORGANIC COMPOUNDS

(75) Inventors: Joaquim Henrique Teles, Otterstadt (DE); Kai Gumlich, Mannheim (DE); Jochen Schäfer, Nürnberg (DE); Steffen Oehlenschläger, Ludwigshafen (DE); Stephan Lamm, Oftersheim (DE); Roland Merten, Weinheim (DE); Martin Schäfer, Grünstadt (DE); Rüdiger Grob, Mackenbach (DE); Uwe Emnet, Doha (QA)

(73) Assignee: BASF SE, Ludwigshafen (DE)

( * ) Notice: Subject to any disclaimer, the term of this patent is extended or adjusted under 35 U.S.C. 154(b) by 574 days.

(21) Appl. No.: 12/674,058

(22) PCT Filed: Aug. 1, 2008

(86) PCT No.: PCT/EP2008/060121
§ 371 (c)(1),
(2), (4) Date: Dec. 16, 2010

(87) PCT Pub. No.: WO2009/024446
PCT Pub. Date: Feb. 26, 2009

(65) Prior Publication Data
US 2011/0087038 A1    Apr. 14, 2011

(30) Foreign Application Priority Data

Aug. 21, 2007  (EP) .................................. 07114711

(51) Int. Cl.
*C07C 51/16*  (2006.01)
*B01J 10/00*  (2006.01)

(52) U.S. Cl.
USPC ........................ 554/134; 422/600; 562/531

(58) Field of Classification Search
USPC ............................ 554/134; 422/600; 562/531
See application file for complete search history.

(56) References Cited

U.S. PATENT DOCUMENTS

| 5,726,321 A | 3/1998 | Bittins et al. |
| 6,479,680 B1 | 11/2002 | Bassler et al. |

(Continued)

FOREIGN PATENT DOCUMENTS

| DE | 19835907 A1 | 2/2000 |
| DE | 19854637 A1 | 5/2000 |
| DE | 19854637 A1 * | 5/2000 |
| DE | 102004021763 A1 | 5/2005 |
| EP | 733401 * | 9/1996 |
| EP | 0733401 A2 | 9/1996 |
| WO | WO-99/54274 A1 | 10/1999 |

(Continued)

OTHER PUBLICATIONS

U.S. Appl. No. 12/674,466, filed Feb. 18, 2010.

*Primary Examiner* — Deborah D Carr
(74) *Attorney, Agent, or Firm* — Novak Druce Connolly Bove + Quigg LLP

(57) ABSTRACT

The invention relates to a process for the oxidation of organic compounds by means of oxygen, in which, in a first step, the organic compound and at least part of the oxygen required for the oxidation are introduced into a first reaction zone which is operated isothermally and with backmixing and, in a second step, the reaction mixture from the first reaction zone is introduced into a second reaction zone which is operated adiabatically. The invention further relates to a reactor for carrying out the process, which comprises at least one isothermal reaction zone (3, 5) and an adiabatic reaction zone (7) which are arranged in a reactor shell (8), with each isothermal reaction zone (3, 5) being configured in the form of a jet loop reactor and the adiabatic reaction zone (7) being configured as a bubble column.

25 Claims, 1 Drawing Sheet

(56) References Cited

U.S. PATENT DOCUMENTS

| | | |
|---|---|---|
| 6,696,582 B2 | 2/2004 | Springer et al. |
| 6,838,061 B1 | 1/2005 | Berg et al. |
| 2006/0047147 A1 * | 3/2006 | Wonders et al. ............. 562/414 |

FOREIGN PATENT DOCUMENTS

| | | |
|---|---|---|
| WO | WO-00/30743 A1 | 6/2000 |
| WO | WO-01/46111 A1 | 6/2001 |
| WO | WO-01/66505 A1 | 9/2001 |

* cited by examiner

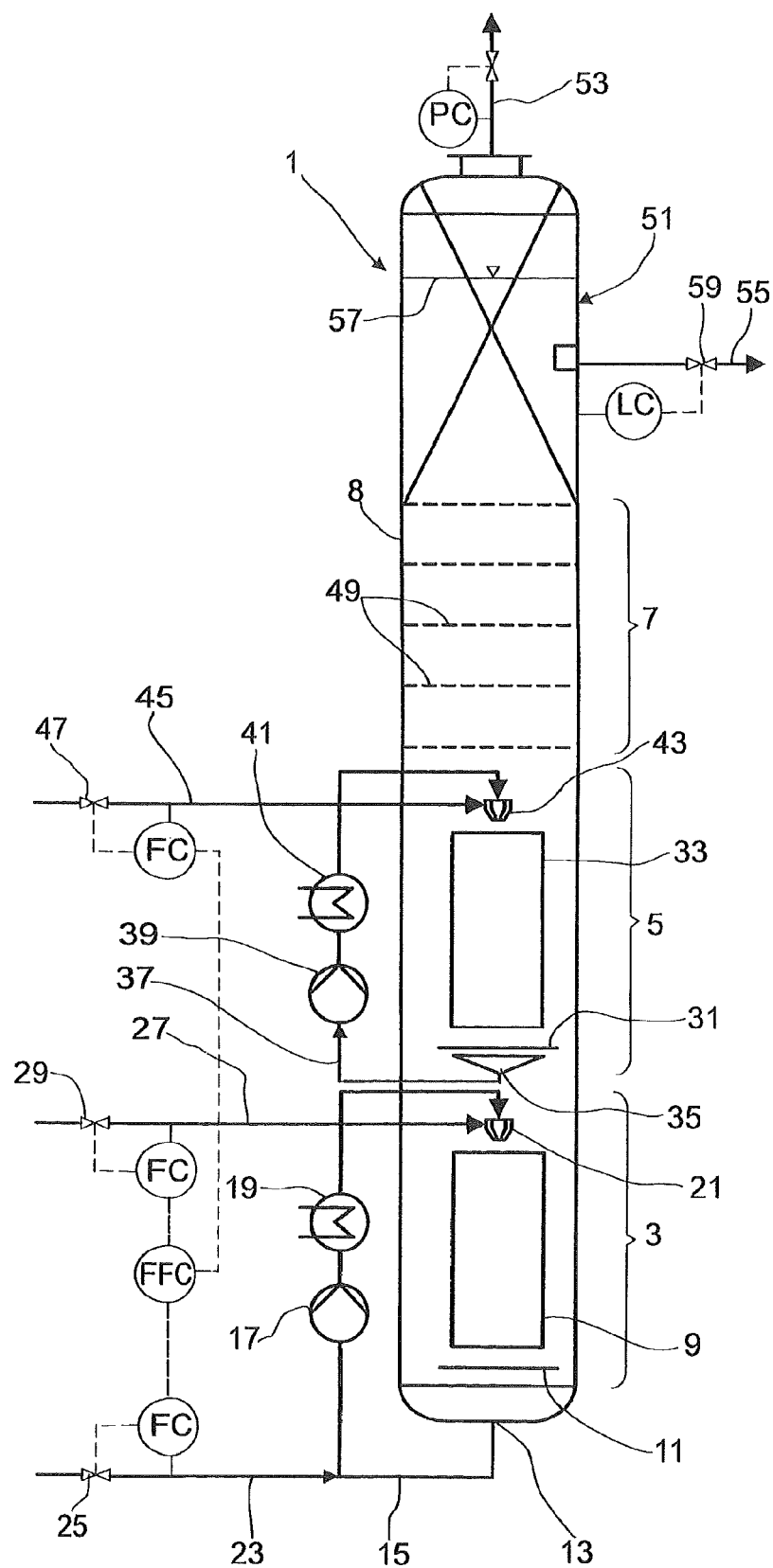

PROCESS AND DEVICE FOR THE OXIDATION OF ORGANIC COMPOUNDS

RELATED APPLICATIONS

This application is a national stage application (under 35 U.S.C. §371) of PCT/EP2008/060121, filed Aug. 1, 2008, which claims benefit of European application 07114711.0, filed Aug. 21, 2007.

The invention relates to a process for the oxidation of organic compounds by means of oxygen. Furthermore, the invention comprises a reactor for carrying out the process.

The process is suitable, for example, for the oxidation of aldehydes to their corresponding acids by means of oxygen.

The preparation of organic acids is known, for example, from WO 99/54274. For this purpose, one or more organic liquids are oxidized by means of essentially pure oxygen or oxygen-enriched air comprising at least 50% of oxygen in a reactor for the oxidation of liquids. The temperature is maintained within a range of ±3° C. about a target temperature. After the reaction, the reaction mixture is worked up. The work-up is carried out by, for example, distillation, solvent extraction, crystallization, evaporation, phase separation, filtration or the like. A loop reactor in which a plug-in tube is comprised in the reactor is used for the reaction. A heat exchanger is accommodated in the space between the plug-in tube and the column wall. The liquid flow in the reactor is produced by means of a stirrer in the plug-in tube.

A loop reactor for carrying out gas-liquid, liquid-liquid or gas-liquid-solid reactions is known from WO-A 00/30743. The reactor comprises a downward-directed jet nozzle which is arranged in the upper region of the reactor and through which the starting materials and the reaction mixture are fed in and also an offtake, preferably in the lower region of the reactor, via which the reaction mixture is introduced into an external circuit and fed to the jet nozzle again by means of a pump. A concentric guide tube which extends essentially over the entire length of the reactor with the exception of the reactor ends is arranged in the reactor. The guide tube has a cross-sectional area in the range from 1/10 to half of the cross-sectional area of the reactor. The jet nozzle is located above the upper end of the guide tube, preferably at a distance of from 1/8 of the guide tube diameter to one guide tube diameter, or dips into the guide tube to a depth of up to a plurality of guide tube diameters. A heat exchanger is integrated into the annular space. The reactor is used, for example, for the preparation of propionic acid from propionaldehyde. For this purpose, the propionaldehyde is oxidized by means of oxygen from air. To achieve an increased conversion, it is stated that a plurality of the reactors can be connected in series.

WO 01/66505 discloses a process for preparing aliphatic carboxylic acids having from 4 to 10 carbon atoms by oxidation of the corresponding aldehydes by means of oxygen or oxygen-comprising gases. The oxidation is carried out in the temperature range from 0 to 100° C. in at least two stages at temperatures which increase from stage to stage. A reactor is provided for each reaction stage. As reactors, tube reactors which may, if appropriate, comprise packing elements, trickle towers comprising packing elements or bubble columns are described by way of example.

A process for the oxidation of an organic substance wherein oxygen, oxygen-enriched or oxygen-comprising air is passed into a liquid in a reaction system, is known from WO 01/46111. The reaction is carried out at a temperature in the range from 20 to 100° C. and a pressure in the range from 0 to 3 bar. Means for achieving mixing of the liquid are provided in the reaction system. To achieve mixing, it is possible to use, for example, stirrers, axial impellers, turbines, injectors, submerged porous diffusers, spargers or surface aerators. Baffles can be accommodated in the reactor.

A disadvantage of the processes known from the prior art is, firstly, that some of these can be operated only as batch processes or semibatch processes. A further disadvantage is that some of the known processes use complicated, therefore expensive, apparatuses. In addition, some of the processes known from the prior art require more than one reactor in order to achieve the desired high conversions.

It is an object of the present invention to provide a continuous process for the oxidation of organic compounds. A further object of the present invention is to provide a reactor in which an oxidation of organic compounds by means of oxygen can be carried out and which can be operated safely when ignitable gas mixtures are formed.

The object is achieved by a process for the oxidation of organic compounds by means of oxygen, which comprises the following steps:
(a) introduction of the organic compound and at least part of the oxygen required for the oxidation into a first reaction zone which is operated isothermally,
(b) introduction of at least part of the reaction mixture from the first reaction zone into a second reaction zone which is operated adiabatically.

The process of the invention is suitable, for example, for the oxidation of hydrocarbons, of olefins, of phenols and of aldehydes by means of oxygen or an oxygen-comprising mixture in which the proportion of oxygen is greater than 50% by volume. Oxidations of hydrocarbons are, for example, the oxidation of cyclohexane to give a mixture comprising cyclohexyl hydroperoxide, cyclohexanone, cyclohexanone and adipic acid, of isobutane to give a mixture comprising tert-butyl hydroperoxide and tert-butanol, of isopentane to give a mixture comprising tert-amyl hydroperoxide and tert-amyl alcohol, of ethylbenzene to give a mixture comprising ethylbenzene hydroperoxide, 1-phenylethanol and acetophenone, of cumene to give a mixture comprising cumene hydroperoxide and 2-phenyl-2-propanol and of p-cumene to give a mixture comprising p-cumene hydroperoxide and 2-(4-tolyl)-2-propanol). Oxidations of olefins are, for example, the oxidation of cyclopentene to give a mixture comprising cyclopentyl hydroperoxide, cyclopentenol and cyclopentenone, of 2,3-dimethyl-2-butene to give a mixture comprising tetramethyloxirane. Oxidations of phenols are, for example, the oxidation of 2,3,6-trimethylphenol to give a mixture comprising trimethylbenzoquinone, of 2,3,5-trimethylphenol to give a mixture comprising trimethylbenzoquinone, of mesitol to give a mixture comprising 2,4,6-trimethyl-4-hydroperoxycyclohexa-2,5-dien-1-one.

However, the process is particularly suitable for the oxidation of aliphatic aldehydes by means of oxygen to form carboxylic acids.

An advantage of the process of the invention is that the aliphatic aldehyde is reacted essentially completely in the oxidation by means of oxygen. For the present purposes, "essentially completely" means that the conversion is greater than 97%, preferably greater than 98%.

The aldehyde used is preferably an aldehyde of the formula

Here, R is $C_1$-$C_{25}$-alkyl, preferably $C_2$-$C_{20}$-alkyl. The alkyl group can be branched or unbranched.

The branched or unbranched $C_1$-$C_{25}$-alkyl group is preferably selected from among ethyl, propyl, isopropyl, n-butyl, sec-butyl, isobutyl, 2-pentyl, 3-pentyl, n-pentyl, n-hexyl, 2-heptyl, 3-heptyl, 4-octyl, 2-methyl-4,4-dimethylpentyl, 2,6-dimethylheptyl, 4-nonyl, 3-methyl-5-octyl.

In a preferred process variant, at least one further reaction zone which is operated isothermally and with backmixing is configured between the first reaction zone which is operated isothermally and with backmixing and the second, adiabatically operated reaction zone. To carry out the reaction, the reaction mixture passes successively through the individual reaction zones. Due to the backmixing, a largely homogeneous concentration distribution is achieved within each isothermally operated reaction zone. When a plurality of reaction zones which are operated isothermally and with backmixing are used, oxygen is preferably introduced into a plurality of the reaction zones which are operated isothermally and with backmixing. Thus, part of the oxygen is introduced into the first reaction zone, as a result of which part of the organic compound is reacted. A further part of the oxygen required is then introduced into each of the further reaction zones which are operated isothermally and with backmixing. Further parts of the aldehyde comprised are then reacted in these. It is possible to introduce part of the oxygen into each of the reaction zones which are operated isothermally and with backmixing. However, it is also possible in the case of a plurality of reaction zones which are operated isothermally and with backmixing for oxygen to be introduced into only part of these reaction zones.

The oxygen required for the reaction can, for example, be introduced in the form of an oxygen-comprising gas or as pure oxygen. If the oxygen is used in the form of an oxygen-comprising gas mixture, this preferably comprises at least 50% by volume of oxygen, more preferably at least 75% by volume of oxygen, particularly preferably at least 90% by volume of oxygen. However, very particular preference is given to using oxygen having a purity of more than 99% by volume. This is also referred to as pure oxygen. If a gas mixture is used, this preferably comprises gases which are inert in respect of the reaction in addition to oxygen. In particular, the gas mixture comprises nitrogen in addition to oxygen. The gas mixture can be, for example, oxygen-enriched air.

In a particularly preferred embodiment, the process for the oxidation of organic compounds comprises two reaction zones which are operated isothermally and with backmixing. Preference is given to introducing at least 60% by volume, more preferably at least 60% by volume and in particular at least 80% by volume, of the total oxygen or oxygen-comprising gas used into the first reaction zone. The remaining oxygen used is introduced in the second reaction stage.

When the process comprises more than two isothermal and backmixed reaction zones and the oxygen or the oxygen-comprising gas is introduced in three reaction stages, preference is likewise given to at least 60% by volume, more preferably at least 60% by volume and in particular at least 80% by volume, of the total oxygen or oxygen-comprising gas used being introduced in the first reaction stage. The second reaction stage is preferably supplied with such an amount of oxygen or oxygen-comprising gas that not more than 10% by volume of the oxygen or oxygen-comprising gas used is introduced in the third reaction stage.

The oxygen is preferably used in excess. This excess is preferably from 1 to 20 mol %, particularly preferably from 2 to 10 mol %, based on the theoretically required amount. The temperature at which the reaction zones which are operated isothermally and with backmixing are operated is preferably in the range from 2 to 140° C., more preferably from 30 to 100° C. The pressure at the outlet of the last reaction zone is preferably in the range from 0.5 to 10 bar, in particular from 1 to 5 bar. Preference is given here to using only one pressure regulator which is located at the outlet of the last reaction zone. Since all reaction zones communicate with one another, this pressure regulator determines the pressure in all reaction zones. In general, the pressure decreases from reaction zone to reaction zone.

When a plurality of reaction zones which are operated isothermally and with backmixing are used, preference is given to the temperature in all the reaction zones which are operated isothermally and with backmixing being the same. For the purposes of the invention, "the same" means that the temperature differences between the average temperatures of the individual reaction zones are not greater than 5° C.

However, it is also possible for the reaction zones which are operated isothermally and with backmixing to be operated in such a way that the temperature increases from reaction zone to reaction zone. The temperature difference between the individual reaction zones is then preferably at least 5° C., more preferably at least 10° C.

For the purposes of the present invention, "operated isothermally" means that the temperature differences within a reaction zone are not greater than 10° C. This temperature difference results from the heat transport to the heat exchanger which is necessary for isothermal operation.

Complete backmixing within the reaction zones which are operated isothermally and with backmixing is achieved, for example, by the at least one reaction zone which is operated isothermally and with backmixing operating according to the principle of a jet loop reactor. For this purpose, part of the reaction mixture is taken off from the reaction zone and reintroduced via a nozzle in the upper region of the reaction zone. This produce circular flow in the reaction zone. The nozzle is preferably arranged axially in the reaction zone. In a preferred embodiment, a plug-in tube around which the reaction mixture flows is comprised in the reaction zone. The heat evolved in the reaction is removed from the reaction mixture by means of a heat exchanger. The heat exchanger can be located within the reaction zone or outside the reaction zone. When the heat exchanger is arranged within the reaction zone, preference is given to, for example, heat exchanger tubes being located between the plug-in tube and the outer wall of the reaction zone. Furthermore, it is also possible for the reaction zone to be cooled at its outer wall. A further possibility is for a heat transfer medium to flow through the plug-in tube and thus cool the reaction zone.

In the case of an external heat exchanger, this is preferably arranged so that the proportion of the reaction mixture which is taken off from the reaction zone and returned via the nozzle in the upper region of the reaction zone is passed through the heat exchanger and thus cooled.

The nozzle through which the reaction mixture is fed into the reaction zone to produce the flow is preferably a two-fluid nozzle. The oxygen required for the reaction is also introduced together with the reaction mixture via this two-fluid nozzle. The use of the two-fluid nozzle results in mixing of the reaction mixture with the oxygen or oxygen-comprising gas, with the oxygen or the oxygen-comprising gas being entrained in the flow. Uniform distribution of the oxygen in the reaction mixture is achieved. The organic compound is also reacted uniformly as a result.

The adiabatically operated reaction zone is preferably not backmixed and configured in the form of a bubble column. The reaction mixture from the last isothermal and backmixed reaction zone flows into the bubble column. This reaction mixture comprises oxygen which has not yet been reacted. The proportion of oxygen in the reaction mixture entering the adiabatic reaction zone is preferably below 10% by volume of the total oxygen used. In the adiabatic reaction zone, the oxygen ascends in the form of bubbles in the reaction mixture. The reaction mixture is mixed by means of the ascending bubbles. As a result, the reaction mixture is in contact with the oxygen and remaining organic compounds are oxidized by means of the oxygen.

The adiabatic reaction zone is preferably provided with internals to suppress backmixing within this zone. Suitable internals are, for example, perforated plates which produce a cascaded bubble column; however, ordered packing or a bed of random packing elements are also suitable. A further task of the internals is to produce uniform distribution of the gas bubbles. The adiabatically operated reaction zone serves as after-reactor to achieve high conversions of the organic compound. The adiabatic zone is preferably insulated well from the surroundings so that no heat can be given off to the surroundings or taken up by them.

In a particularly preferred embodiment, all reaction zones are accommodated in a common reactor shell. In this case, the reaction zones are preferably arranged above one another, with the first reaction zone which is operated isothermally and with backmixing being located at the bottom and the adiabatic reaction zone being located at the top. The individual reaction zones are preferably separated from one another by perforated plates. This arrangement ensures that unconsumed oxygen goes from one reaction zone directly into the next reaction zone.

The invention further relates to a reactor for carrying out the process, which comprises at least one isothermal reaction zone and an adiabatic reaction zone which are arranged in a reactor shell, wherein each isothermal reaction zone is configured in the form of a jet loop reactor and the adiabatic reaction zone is configured as a bubble column.

Each of the isothermal reaction zones which are configured in the form of a jet loop reactor preferably comprises a plug-in tube. This is configured so that the liquid can flow around the plug-in tube within the reaction zone. Uniform flow around the plug-in tube is achieved by the plug-in tube being positioned coaxially to the reactor shell. The liquid reaction medium is introduced at the upper end or the lower end of the plug-in tube. An impingement plate is arranged at the end of the plug-in tube opposite the input end. The liquid flows via the introduction device into the plug-in tube, flows through the latter and impinges on the impingement plate. The liquid is deflected by the impingement plate and flows back along the outside of the plug-in tube in the opposite direction in the annular space formed between the plug-in tube and the reactor shell. Loop flow results. After the first reaction zone, the liquid enters the next reaction zone. In a preferred embodiment, two isothermal reaction zones which are each configured in the form of a jet loop reactor with plug-in tube and impingement plate are comprised in the reactor shell. The two isothermal reaction zones configured in the form of the jet loop reactor are arranged above one another in the common reactor shell.

To be able to operate the isothermal reaction zones as jet loop reactors, these preferably have an external liquid circuit. Here, a liquid offtake point is preferably provided in the lower region of the reaction zone and a liquid introduction device is provided in the upper region of the reaction zone. The liquid introduction device is preferably a nozzle which is located centrally above the plug-in tube in the reaction zone. A pump by means of which liquid is drawn in from the reaction zone is preferably provided in the liquid circuit. This liquid is then returned via the nozzle to the reaction zone. The liquid is squirted into the reaction zone under increased pressure and preferably at high velocity so that circular flow results. The flow velocity in the circular flow is preferably so great that gas bubbles are entrained with the flow.

To control the temperature of the reaction medium, the liquid circuit preferably further comprises at least one heat exchanger. The reaction medium flowing through the heat exchanger can be heated/cooled in the heat exchanger. The temperature in the reaction zone can be set in this way.

In a preferred embodiment, the nozzle by means of which the liquid from the liquid circuit is fed into the reaction zone is a two-fluid nozzle via which the liquid and oxygen can be introduced into the reaction zone. In the case of a reactor having two isothermally operated reaction zones, preference is given to introducing at least 70% by volume, more preferably at least 80% by volume, of the oxygen used into the first reaction zone. The remaining oxygen is introduced in the second reaction zone. When a third isothermal reaction zone is provided, the amount of oxygen introduced into the third reaction zone is preferably less than 10% by volume of the oxygen used.

Apart from the embodiment in which the nozzle is located at the upper end of the plug-in tube and the impingement plate is located at the lower end of the plug-in tube, it is also possible for the nozzle to be located at the lower end of the plug-in tube and the impingement plate to be located at the upper end of the plug-in tube. This leads to the reaction medium flowing upward in the plug-in tube and downward around the plug-in tube. However, preference is given to the arrangement in which the nozzle is located above the plug-in tube and the impingement plate is located below the plug-in tube, so that flow occurs from the top downward within the plug-in tube and from the bottom upward outside the plug-in tube. The advantage of this embodiment is that the gas bubbles have to cover a longer distance before they flow into the next reaction zone and thus have a greater average residence time. As a result of this greater residence time of the gas, the achievable conversion is higher in the case of a downward-directed nozzle than in the case of an upward-directed nozzle.

As an alternative to the embodiment in which the heat exchanger is accommodated in the liquid circuit, it is also possible for the heat exchanger to be arranged, for example, in the annular space, i.e. between the column wall and the plug-in tube. Suitable heat exchangers are, for example, heat exchanger tubes through which a temperature-controlled medium flows. However, it is also possible to use any heat exchanger known to those skilled in the art by means of which the temperature in the reaction zone can be regulated.

When using an external heat exchanger located in the liquid circuit, it is also possible to use any heat exchanger known to those skilled in the art. It is thus possible to use, for example, shell-and-tube heat exchangers, plate heat exchangers, helical heat exchangers.

The organic compound to be oxidized is preferably fed into the liquid circuit of the first reaction zone. However, in the case of a plurality of isothermally operated reaction zones, it is also possible for part of the organic compound to be fed into the liquid circuit of the first reaction zone and further parts to be fed into the liquid circuits of the further reaction zones. It is possible here for part of the organic compound to be fed into each reaction zone or it is also possible for the organic compound to be fed into only some of the isothermally operated reaction zones. However, particular preference is given to introducing the organic compound which is to be oxidized in the reactor into only the first reaction zone.

The adiabatic reaction zone preferably comprises internals. Suitable internals are, for example, perforated plates or sieve trays in order to produce a cascaded bubble column.

However, it is also possible, as an alternative, for ordered packing or a bed to be comprised in the adiabatic reaction zone.

To separate the gas and liquid of the reaction medium from one another, the adiabatic reaction zone is preferably followed by a further zone in which gas and liquid are separated from one another to form a continuous gas phase. In addition, the pressure rating of the reactor is selected so that the reactor can survive a pressure peak occurring in the event of ignition without damage. To reduce the consequences of a possible explosion in the gas phase, this further zone preferably comprises a bed or ordered packing. The gas phase generally comprises oxygen since this is used in excess as oxidant. It can further comprise carbon monoxide, carbon dioxide and organic compounds. Owing to the organic compounds which may be comprised, it is possible for the gas phase to be capable of ignition.

As ordered packing or bed in the further zone following the adiabatic reaction zone, it is possible to use any bed or ordered packing known to those skilled in the art. Thus, for example, structured packings or beds of random packing elements are conceivable. Suitable structured packings or packing elements are known to those skilled in the art and are commercially available. Preference is given to using Raschig rings or Pall rings.

As an alternative to the embodiment in which the adiabatic reaction zone is followed by a further zone for gas-liquid phase separation, it is also possible for gas-liquid separation to occur in an additional apparatus. A suitable additional apparatus is, for example, a column comprising ordered packing or random packing elements.

In a preferred embodiment, the reaction mixture is cooled before gas-liquid separation is carried out. The temperature to which the reaction mixture is cooled is preferably below the flashpoint of the liquid. This prevents ignitable gas mixtures from being formed.

In a preferred embodiment, the reactor is used for preparing an organic acid by oxidation of the corresponding aldehyde by means of oxygen. The aldehyde is preferably selected from among propionaldehyde, butyraldehyde, isobutyraldehyde, valeraldehyde, 2-methylbutyraldehyde, 3-methylbutyraldehyde (isovaleraldehyde), 2-ethylbutyraldehyde, n-hexanal, 2-methylvaleraldehyde, n-heptanal, 2-ethylhexanal, n-nonanal, 2-propylheptanal, 2-propyl-4-methylhexanal, 3,5,5-trimethylhexanal and 3,7-dimethyloctanal. The corresponding acids which are prepared by oxidation of these aldehydes by means of oxygen are propionic acid, butyric acid, isobutyric acid, valeric acid, 2-methylbutyric acid, isovaleric acid, 2-methylbutyric acid, 3-methylbutyric acid (isovaleric acid), 2-ethylbutyric acid, n-hexanoic acid, 2-methylvaleric acid, n-heptanoic acid, 2-ethylhexanoic acid, n-nonanoic acid, 2-propylheptanoic acid, 2-propyl-4-methylhexanoic acid, 3,5,5-trimethylhexanoic acid and 3,7-dimethyloctanoic acid. It is likewise possible to oxidize mixtures of two or more aldehydes, for example aldehyde mixtures formed in the hydroformylation of olefins.

Furthermore, the reaction is also suitable for carrying out oxidations of hydrocarbons, olefins or phenols by means of oxygen or an oxygen-comprising mixture having an oxygen content of more than 50% by volume. Examples of suitable oxidations have been mentioned above.

The invention is illustrated below with the aid of a drawing.

The single FIGURE schematically shows a reactor configured according to the invention which has two isothermally operated reaction zones and an adiabatically operated reaction zone.

A reactor 1 configured according to the invention comprises an isothermal reaction zone 3, a second isothermal reaction zone 5 and an adiabatic reaction zone 7. The first isothermal reaction zone 3 and the second isothermal reaction zone 5 are each configured as jet loop reactors. The first isothermal reaction zone 3, the second isothermal reaction zone 5 and the adiabatic reaction zone 7 are accommodated in a common reactor shell 8.

The first reaction zone 3 comprises a first plug-in tube 9 through which the reaction medium flows. A first impingement plate 11 is positioned below the first plug-in tube 9. Liquid which flows through the first plug-in tube 9 impinges on the first impingement plate 11 and is deflected. A liquid offtake point 13 via which reaction medium can be taken off from the first isothermal reaction zone 3 is provided below the first impingement plate 11.

The reaction medium taken off at the liquid offtake point 13 is introduced into a first liquid circuit 15. A first pump 17 is accommodated in the first liquid circuit 15 and circulates the liquid. In the embodiment shown here, the first pump 17 is followed by a first heat exchanger 19. In the first heat exchanger 19, the temperature of the reaction medium which is circulated through the first liquid circuit 15 is regulated. In this way, a uniform temperature is achieved in the first isothermal reaction zone 3. The liquid from the first liquid circuit 15 is returned via a liquid introduction device 21 to the first isothermal reaction zone 3. The liquid introduction device 21 is preferably a nozzle. The liquid introduced is squirted at high velocity into the first reaction zone 3. This results in flow through the first plug-in tube. Owing to the high velocity of the liquid squirted in via the nozzle 21, the liquid surrounding the liquid introduction device 21 is also entrained. Loop flow around the plug-in tube 9 is established. Deflection is effected by the liquid which flows through the plug-in tube 9 impinging on the impingement plate 11 and being deflected there.

The organic compound which is to be oxidized in the reactor is introduced via a liquid inlet 23 which opens into the first liquid circuit 15. The amount of organic compound introduced via the liquid inlet 23 into the first liquid circuit 15 can be set via a valve 25 shown here.

The liquid introduction device 21 in the embodiment shown here is a two-fluid nozzle. Part of the oxygen required for the reaction is also introduced via the two-fluid nozzle. For this purpose, the liquid introduction device 21 is connected to a gas feed line 27. Oxygen or an oxygen-comprising gas is fed to the reactor 1 via the gas feed line 27. The oxygen-comprising gas is, for example, oxygen-enriched air or pure oxygen. The oxygen-comprising gas preferably comprises at least 50% by volume of oxygen, more preferably at least 75% by volume of oxygen and in particular more than 90% by volume of oxygen. The oxygen-comprising gas is very particularly preferably pure oxygen, i.e. a gas mixture having an oxygen content of more than 99% by volume.

Preference is given to at least 70% by volume, more preferably at least 80% by volume, of the oxygen required for the reaction being introduced via the gas feed line 27. The amount of oxygen-comprising gas introduced is set via a second valve 29.

Part of the reaction medium comprised in the first isothermal reaction zone 3 flows past a second impingement plate 31 into the second isothermal reaction zone 5. The second isothermal reaction zone 5 is constructed like the first isothermal reaction zone 3 and comprises a second plug-in tube 33 through which the reaction medium flows. The reaction medium impinges on the second impingement plate 31 and is deflected there. This results in loop flow around the plug-in tube 33. Part of the reaction medium is taken off from the second isothermal reaction zone 5 via a second liquid offtake point 35 and fed to a second liquid circuit 37. The reaction medium is circulated in the second liquid circuit 37 by means of a second pump 39. The second pump 39 is followed by a second heat exchanger 41 in which the temperature of the reaction medium which flows through the second liquid circuit 37 is regulated. In this way, isothermal reaction conditions are achieved in the second isothermal reaction zone 5. The liquid which flows through the second liquid circuit 27 is fed via a second liquid introduction device 43 into the second isothermal reaction zone 5. The second liquid introduction device 43 is preferably likewise a two-fluid nozzle. The remainder of the oxygen required for the reaction is introduced via the second liquid introduction device 42 configured as a two-fluid nozzle. For this purpose, the second liquid introduction device 43 is connected to a second gas feed line 45. The amount of oxygen introduced via the second gas feed line 45 is set by means of a third valve 47.

In the embodiment shown here, the first liquid introduction device 21 and the second liquid introduction device 43 are centered axially above the first plug-in tube 9 and the second plug-in tube 33, respectively. This leads to the liquid flowing downward in each case in the plug-in tube 9, 33 and impinging on the impingement plate 11, 31. Here, the liquid is deflected and subsequently transported upward along the outside of the plug-in tube 9, 33 between the plug-in tube 9, 33 and the reactor shell 8.

However, as an alternative to the embodiment shown here, it is also possible for the first liquid introduction device 21 and the second liquid introduction device 43 each to be located below the plug-in tube 9, 33 and the impingement plate 11, 31 to be located above the plug-in tube. In this case, the liquid flows through the plug-in tube from the bottom upward, is deflected at the impingement plate 11, 31 and flows downward again on the outside between the plug-in tube 9, 33 and the column 8.

As an alternative to the embodiment shown here, in which the heat exchanger 19, 41 is located in the liquid circuit 15, 37, it is also possible to position a first heat exchanger in the space between the first plug-in tube 9 and the reactor shell 8 and position a second heat exchanger in the space between the second plug-in tube 33 and the reactor shell 8.

The second isothermal reaction zone 5 is followed by the adiabatic reaction zone 7. The adiabatic reaction zone 7 preferably comprises internals. In the embodiment shown here, these are sieve trays 49. The reaction medium which flows into the adiabatic reaction zone 7 comprises oxygen which has not yet been reacted. This is present in the form of bubbles. Since no circulation takes place in the adiabatic reaction zone 7 but instead the reaction medium flows from the bottom upward, the gas bubbles comprised in the reaction medium ascend. The adiabatic reaction zone 7 is thus operated in the form of a bubble column. A cascaded bubble column is produced by the sieve trays 49 comprised in the adiabatic reaction zone 7.

As an alternative to the sieve trays 49, it is also possible to use perforated plates or any other trays known to those skilled in the art. It is also possible to provide ordered packing or a bed as internals.

The adiabatic reaction zone 7 is followed, in the embodiment shown here, by a further zone 51. The further zone 51 serves to separate gas and liquid from one another. The zone 51 preferably comprises ordered packing or a bed. This serves to reduce the consequences of a possible explosion in the gas phase. The excess gas is taken off from the reactor 1 via a gas offtake 53. At the same time, the pressure in the reactor can be set via the gas offtake 53.

The liquid is taken off from the reactor via a side offtake 55. This is located in the region of the further zone 51. During operation, the entire reactor is flooded with the liquid reaction medium. The liquid level is indicated by the phase boundary line 57.

The amount of liquid taken off via the side offtake 55 can be set via a valve 59. At the same time, the liquid level in the reactor is regulated by means of this.

EXAMPLE 1

Oxidation of Valeraldehyde to Valeric Acid

A reactor as shown in FIG. 1 is used for the oxidation of valeraldehyde to valeric acid. The reactor has the shape of an upright cylinder having a diameter of about 940 mm and comprises two isothermal stages and an adiabatic stage. The first isothermal stage, i.e. the first from the bottom, has a total length, measured between the bottom reactor flange and the two-fluid nozzle of the first stage, of about 5000 mm. The plug-in tube having a diameter of 500 mm and a length of 4100 mm is installed axially. Immediately above the plug-in tube, the two-fluid nozzle of the first stage is centered axially, pointing downward. An axially centered and horizontal impingement plate having a diameter of 620 mm is located underneath the plug-in tube. The contents of the reactor are drawn in by a circulation pump via a bottom outlet below the impingement plate. The fresh valeraldehyde is fed in on the suction side of the pump. A shell-and-tube heat exchanger operated using cooling water is installed on the pressure side of the circulation pump to remove the heat of reaction generated in the first stage. The stream leaving the heat exchanger is conveyed to the two-fluid nozzle. The oxygen required for oxidation in the first stage is conveyed as gas having an oxygen content of >99% likewise to the two-fluid nozzle. These elements form the first isothermal stage of the reactor.

Directly above the first stage, there is the second isothermal stage. This has essentially the same elements and dimensions as the first stage, but the contents of the reactor of the second stage are drawn off via a funnel below the impingement plate of the second stage, the heat exchanger and the circulation pump of the second stage are smaller corresponding to the lower demands and the two-fluid nozzle of the second stage is dimensioned so that it can be operated without introduction of oxygen.

Above the second isothermal stage, there is the adiabatic stage. This stage comprises an empty tube which has a length of 5800 mm and is divided by perforated plates at intervals of about 1400 mm. These perforated plates serve, firstly, to prevent backflow and, secondly, to redistribute the oxygen still present in the liquid.

Above the adiabatic stage, there is a disengagement zone in which gas and liquid can separate. For safety reasons, the disengagement zone or at least the space comprising a continuous gas phase is filled with Raschig rings having a diameter of 10 mm. The gas is taken off under pressure regulation at the top of the reactor and is passed to offgas treatment. The liquid is taken off under level control via a side port and passed to work-up.

The reactor is firstly filled with valeric acid and the circulation pumps are set into operation. The circulation stream in the first stage is set to about 193 m$^3$/h. The pressure difference over the circulation pump is about 4 bar. The circulation stream in the second stage is set to about 92 m$^3$/h. The pressure difference over the circulation pump of the second stage is about 3 bar. The contents of the reactor were then heated to 60° C. The pressure regulator at the top of the reactor is subsequently brought into operation and set to 2 bar abs. The level-regulated offtake of product is also set into operation. The metered addition of $O_2$ and valeraldehyde is then increased stepwise to the final value. In the steady state, 1125 kg/h of valeraldehyde are fed into the circuit of the first isothermal stage. The valeraldehyde used comes from the hydroformylation of butene and is purified by distillation. The proportion of 2-methylbutanal is less than 1% by weight. 187 kg/h of $O_2$ are metered in via the two-fluid nozzle of the first stage. 33 kg/h of $O_2$ are metered in via the two-fluid nozzle of the second stage.

After the steady state has been reached, samples are taken. The valeraldehyde conversion in the first isothermal stage is 88.5, determined by gas-chromatographic analysis of samples taken from the circulation stream of the first stage. The valeraldehyde conversion in the second isothermal stage is 98.2%, determined by gas-chromatographic analysis of samples taken from the circulation stream of the second stage. The valeraldehyde conversion at the reactor outlet is 99.94%. The selectivity to valeric acid based on valeraldehyde is 98.7%, determined by gas-chromatographic analysis of the liquid product leaving the reactor.

By-products comprised in the liquid product are, inter alia, n-butyl formate, n-butanol, butyric acid, n-octane, levulinic acid, butyl valerate, pentyl valerate and n-valeric anhydride. The offgas comprises 0.69% by volume of organic material and is accordingly not capable of ignition. Apart from $O_2$ and valeric acid, the gas phase further comprises $CO_2$, CO, $H_2$, butane and formic acid.

EXAMPLE 2

Oxidation of Valeraldehyde to Valeric Acid

The procedure of example 1 is repeated with 1125 kg/h of aldehyde being introduced, but the total amount of 220 kg/h of $O_2$ is introduced into the first isothermal stage.

The valeraldehyde conversion in the first isothermal stage is 92.5%. The valeraldehyde conversion in the second isothermal stage is 98.8%. The valeraldehyde conversion at the reactor outlet is 99.93%, determined by gas-chromatographic analysis of the liquid product leaving the reactor. The selectivity to valeric acid based on valeraldehyde is 98.7%.

EXAMPLE 3

Oxidation of 3-Methylbutanal to 3-Methylbutyric Acid

The procedure of example 2 is repeated, i.e. 1125 kg/h of aldehyde are introduced and the total amount of 220 kg/h of $O_2$ is introduced in the first stage, but 3-methylbutanal is used instead of valeraldehyde. The 3-methylbutanal is obtained by hydroformylation of isobutene and purified by distillation. It comprises at least 99% by weight of 3-methylbutanal. For the start-up, the reactor is filled with 3-methylbutyric acid rather than with valeric acid.

The 3-methylbutanal conversion in the first isothermal stage is 97.4%. The 3-methylbutanal conversion in the second isothermal stage is 99.8%. The 3-methylbutanal conversion at the reactor outlet is 99.99%. The selectivity to 3-methylbutyric acid based on 3-methylbutanal is 97.1%.

By-products comprised in the liquid product are, inter alia, isobutyl formate, isobutanol, isobutyric acid, 2,4-dimethylpentane, 2,5-dimethylhexane, 2-butanone, diisobutyl ether and 3-methylbutyric anhydride. Apart from $O_2$ and 3-methylbutyric acid, the gas phase further comprises $CO_2$, CO, $H_2$, isobutane, isobutene, acetaldehyde, isopropyl formate, tert-butyl formate, isobutyl formate and formic acid.

EXAMPLE 4

Oxidation of Isononanal to Isononanoic Acid

The procedure of example 2 is repeated, i.e. 1125 kg/h of aldehyde are introduced and the total amount of 133 kg/h of $O_2$ is introduced in the first stage, but isononanal is used instead of valeraldehyde. The isononanal is obtained by hydroformylation of diisobutylene and purified by distillation. It comprises at least 99% of $C_9$-aldehydes with 3,5,5-trimethylhexanal as main component. For the start-up, the reactor is filled with isononanoic acid rather than with valeric acid.

The isononanal conversion in the first isothermal stage is 96.7%. The isononanal conversion in the second isothermal stage is 99.7%. The isononanal conversion at the reactor outlet is 99.98%.

By-products comprised in the liquid product are, inter alia, 2,4,4-trimethylpentanol formate, 2,4,4-trimethylpentanol, trimethylpentane and isononyl formate. The offgas comprises 0.02% by volume of organic material and is accordingly not ignitable. Apart from $O_2$ and isononanoic acid, the gas phase further comprises $CO_2$, CO, $H_2$, 2,4,4-trimethylpentane, etc.

EXAMPLE 5

Oxidation of Propionaldehyde to Propionic Acid

The procedure of example 2 is repeated, i.e. 1125 kg/h of aldehyde are introduced and the total amount of 326 kg/h of $O_2$ is introduced in the first stage, but propionaldehyde is used instead of valeraldehyde. The reaction temperature in the two isothermal stages is 75° C. The propionaldehyde is obtained by hydroformylation of ethylene and purified by distillation. For the start-up, the reactor is filled with propionic acid rather than valeric acid. The pressure regulator at the top of the reactor is set to a pressure of 2 bar abs.

The propionaldehyde conversion in the first isothermal stage is 93.7%. The propionaldehyde conversion in the second isothermal stage is 98.5%. The propionaldehyde conversion at the reactor outlet is 99.8%.

By-products comprised in the liquid product are, inter alia, ethyl formate, ethanol, acetic acid. Apart from $O_2$ and propionic acid, the gas phase further comprises $CO_2$, CO, $H_2$, ethane.

LIST OF REFERENCE NUMERALS 1 reactor
3 first isothermal reaction zone
5 second isothermal reaction zone
7 adiabatic reaction zone
8 reactor shell
9 first plug-in tube
11 first impingement plate
13 liquid offtake point
15 first liquid circuit
17 first pump
19 first heat exchanger
21 liquid introduction device
23 liquid inlet
25 valve
27 gas feed line
29 second valve 31 second impingement plate
33 second plug-in tube
35 second liquid offtake point
37 second liquid circuit
39 second pump
41 second heat exchanger
43 second liquid introduction device
45 second gas feed line
47 third valve
49 sieve tray
51 further zone
53 gas offtake
55 side offtake
57 phase boundary line
59 valve

The invention claimed is:

1. A process for the oxidation of organic compounds by means of oxygen, which comprises the following steps:
    (a) introduction of the organic compound and at least part of the oxygen required for the oxidation into a first reaction zone which is operated isothermally and with backmixing,
    (b) introduction of at least part of the reaction mixture from the first reaction zone into a second reaction zone which is operated adiabatically.

2. The process according to claim 1, wherein at least one further reaction zone which is operated isothermally and with backmixing is configured between the first reaction zone and the second reaction zone.

3. The process according to claim 2, wherein the part of the oxygen required for the reaction which has not been introduced in step (a) is introduced into the reaction mixture in the at least one further reaction zone which is operated isothermally and with backmixing.

4. The process according to claim 1, wherein the at least one reaction zone which is operated isothermally and with backmixing operates according to the principle of a loop reactor, with part of the reaction mixture being taken off from the reaction zone and reintroduced via a nozzle in the upper region of the reaction zone, thus producing circular flow in the reaction zone.

5. The process according to claim 4, wherein the part of the reaction mixture which is taken off from the reaction zone which is operated isothermally and with backmixing and reintroduced via the nozzle in the upper region of the reaction zone is conveyed through a heat exchanger in order to achieve isothermal conditions in the reaction zone.

6. The process according to claim 1, wherein the adiabatically operated reaction zone is configured in the form of a bubble column.

7. The process according to claim 6, wherein the adiabatically operated reaction zone comprises at least one sieve tray or perforated plate by means of which the flow of the reaction mixture through the adiabatically operated reaction zone is set.

8. The process according to claim 1, wherein all reaction zones are accommodated in a common reactor shell.

9. The process according to claim 1, wherein all reaction zones are accommodated in a common reactor shell.

10. The process according to claim 1, wherein the organic compound is an aldehyde which is oxidized to its corresponding acid.

11. The process according to claim 9, wherein the aldehyde is selected from among propionaldehyde, butyraldehyde, isobutyraldehyde, valeraldehyde, 2-methylbutyraldehyde, isovaleraldehyde, 2-ethylbutyraldehyde, n-hexanal, n-heptanal, 2-ethylhexanal, 2-propylheptanal, 3,5,5-trimethylhexanal and 3,7-dimethyloctanal.

12. A reactor for carrying out the process according to claim 1, which comprises at least one isothermal reaction zone (3, 5) and an adiabatic reaction zone (7) which are arranged in a reactor shell (8), wherein each isothermal reaction zone (3, 5) is configured in the form of a jet loop reactor and the adiabatic reaction zone (7) is configured as a bubble column.

13. The reactor according to claim 12, wherein the reactor shell (8) comprises two isothermal reaction zones (3, 5) which are configured in the form of a jet loop reactor and are arranged above one another in the reactor shell (8).

14. The reactor according to claim 12, wherein an impingement plate (11, 31) is accommodated in the lower region of each of the individual isothermal reaction zones (3, 5) configured in the form of a jet loop reactor.

15. The reactor according to claim 12, wherein the at least one isothermal reaction zone (3, 5) configured as a jet loop reactor has an external liquid circuit (15, 37) and a liquid offtake point (13, 35) is located in the lower region of the isothermal reaction zone (3, 5) and a liquid introduction device (21, 43) is located in the upper region of the isothermal reaction zone (3, 5).

16. The reactor according to claim 15, wherein the liquid introduction device (21, 43) is a nozzle which is located centrally in the upper region of the isothermal reaction zone (3, 5).

17. The reactor according to claim 16, wherein the nozzle is a two-fluid nozzle via which liquid and oxygen can be introduced into the isothermal reaction zone (3, 5).

18. The reactor according to claim 16, wherein a heat exchanger (19, 41) is comprised in the external liquid circuit (15, 37).

19. The reactor according to claim 16, wherein a heat exchanger is accommodated in the outer region of the isothermal reaction zone (3, 5) configured in the form of a jet loop reactor between a plug-in tube (9, 33) and the reactor shell (8).

20. The reactor according to claim 16, wherein a liquid inlet (23) for a starting material opens into the liquid circuit (15) of the first isothermal reaction zone (3).

21. The reactor according to claim 16, wherein perforated plates or sieve trays (49) are comprised in the adiabatic reaction zone (7).

22. The reactor according to claim 16, wherein the adiabatic reaction zone (7) is followed by a further zone (51) for phase separation, with the further zone (51) comprising a bed or ordered packing.

23. The reactor according to claim 22, wherein the reaction zones (3, 5, 7) are arranged above one another, with the first isothermal reaction zone (3) being located at the bottom and the adiabatic reaction zone (7) being located at the top in the reactor shell (8).

24. A method for preparing an organic acid by oxidation of the corresponding aldehyde by means of oxygen using the reactor according to claim 22.

25. The method according to claim 24, wherein the aldehyde is selected from among propionaldehyde, butyraldehyde, isobutyraldehyde, valeraldehyde, 2-methylbutyraldehyde, isovaleraldehyde, 2-ethylbutyraldehyde, n-hexanal, n-heptanal, 2-ethylhexanal, 2-propylheptanal, 3,5,5-trimethylhexanal and 3,7-dimethyloctanal.

* * * * *

UNITED STATES PATENT AND TRADEMARK OFFICE
CERTIFICATE OF CORRECTION

| | | | |
|---|---|---|---|
| PATENT NO. | : | 8,575,379 B2 | Page 1 of 1 |
| APPLICATION NO. | : | 12/674058 | |
| DATED | : | November 5, 2013 | |
| INVENTOR(S) | : | Teles et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 874 days.

Signed and Sealed this
Twenty-second Day of September, 2015

Michelle K. Lee
*Director of the United States Patent and Trademark Office*